United States Patent
Park et al.

(10) Patent No.: US 7,050,163 B2
(45) Date of Patent: May 23, 2006

(54) APPARATUS FOR SOLUTION COMPONENT ANALYSIS AND FABRICATING METHOD THEREOF

(75) Inventors: Kwang Bum Park, Pyeongtaek-si (KR); Joon Shik Park, Gunpo-si (KR); Kyu Sik Shin, Pyeongtaek-si (KR); Hyo Derk Park, Pyeongtaek-si (KR)

(73) Assignee: Korea Electronics Technology Institute, Kyunggi-do (KR)

( * ) Notice: Subject to any disclaimer, the term of this patent is extended or adjusted under 35 U.S.C. 154(b) by 0 days.

(21) Appl. No.: 10/977,757

(22) Filed: Oct. 28, 2004

(65) Prior Publication Data
US 2005/0140972 A1 Jun. 30, 2005

(30) Foreign Application Priority Data
Dec. 29, 2003 (KR) .................. 10-2003-0098927

(51) Int. Cl.
*G01N 1/10* (2006.01)
(52) U.S. Cl. .................................. 356/246
(58) Field of Classification Search ............ None
See application file for complete search history.

(56) References Cited

U.S. PATENT DOCUMENTS

| 6,767,706 B1 * | 7/2004 | Quake et al. ................. 435/6 |
| 6,875,619 B1 * | 4/2005 | Blackburn ................. 436/514 |

* cited by examiner

*Primary Examiner*—Tu T. Nguyen
(74) *Attorney, Agent, or Firm*—Lee, Hong, Degerman, Kang & Schmadeka

(57) ABSTRACT

The present invention provides an apparatus for solution component analysis and fabricating method thereof, by which a mixing channel, reaction channel, and measurement channel are formed as continuous micro-grooves on one substrate to implement the miniature apparatus for analyzing solution components, by which the apparatus is provided with portability facilitating access to a spot outside a laboratory to perform an instant sample analysis, and by which an optical system configuration for sample analysis can be simplified in a manner of facilitating an optical transfer by forming a transparent silicon oxide ($SiO_2$) layer between a micro channel of the apparatus and an optical fiber to insert the optical fiber therein.

11 Claims, 6 Drawing Sheets

– 1 –

APPARATUS FOR SOLUTION COMPONENT ANALYSIS AND FABRICATING METHOD THEREOF

BACKGROUND OF THE INVENTION

1. Field of the Invention

The present invention relates to an apparatus for analyzing solution components and fabricating method thereof, and more particularly, to an apparatus for solution component analysis and fabricating method thereof, by which a mixing channel, reaction channel, and measurement channel are formed as continuous micro-grooves on one substrate to implement the miniature apparatus for analyzing solution components and by which the apparatus is provided with portability for instant sample analysis.

The solution component analyzing apparatus according to the present invention is to decide the sort of an unknown solution component using the Beer-Lambert Principle and to measure a concentration of the solution component.

2. Discussion of the Related Art

FIG. 1 is a schematic diagram of a solution component analyzing apparatus according to prior art.

Referring to FIG. 1, a solution component analyzing apparatus according to prior art comprises a light source 10, a monochromator 20 separating a light of the light source 10 into multi-wavelength lights, a transparent sample vessel 30 transmitting the multi-wavelength lights separated by the monochromator 20 and holding a sample solution therein, and a light-receiving unit 50 receiving the multi-wavelength lights transmitted through the transparent sample vessel 30 via an optical system 40 to measure a light intensity.

The light source 10 employs such a light source as a xenon lamp, tungsten-halogen lamp, and the like, which emit a continuous light. The light emitted from the light source 10 is separated into the multi-wavelength lights using the monochromator having a diffraction grid or an optical filter.

The separated multi-wavelength lights pass through the transparent sample vessel 30 filled up with a measurement sample solution.

In doing so, some of the multi-wavelength lights passing through the transparent sample vessel 30 are absorbed in a measurement sample solution component, whereas the others of the multi-wavelength lights pass through the transparent sample vessel 30. And, a light-receiving sensor of the light-receiving unit 50 measures the variation of the light intensity for each wavelength band on the multi-wavelength lights having passed through the transparent sample vessel 30.

FIG. 2 is an exemplary graph of measurement by a solution component analyzer according to prior art.

Referring to FIG. 2, a light having a specific wavelength band is absorbed in a sample solution so that the light-receiving unit 50 measures a variation that a light intensity decreases like 'a'. A pattern of a photo-absorption spectrum can be more complicated according to the sample solution. And, a component and concentration within the sample solution can be determined using the pattern of the photo-absorption spectrum and the light intensity variation of the pattern.

However, the prior art solution component analyzer comprising the light source, monochromator, sample vessel, light-receiving sensor, and the like, increases in its volume and weight, thereby failing to facilitate its portability.

And, in order to prepare the sample solution for measuring the component within the solution and the concentration of the component, the related art solution component analyzer additionally needs a mixer or reactor for mixing additives to meet acidity (pH) of the sample solution or catalyst additives for accelerating reaction. Moreover, the prior art solution component analyzer occasionally needs such an equipment as a separator for separating only the measurement sample solution. For such reasons, it is difficult to instantly analyze the components of a solution collected on the spot outside a laboratory equipped with the prior art solution component analyzer. And, it takes a considerably long period of time to analyze the components.

SUMMARY OF THE INVENTION

Accordingly, the present invention is directed to an apparatus for solution component analysis and fabricating method thereof that substantially obviate one or more problems due to limitations and disadvantages of the related art.

An object of the present invention is to provide an apparatus for solution component analysis and fabricating method thereof, by which a mixing channel, reaction channel, and measurement channel are formed as continuous micro-grooves on one substrate to implement the miniature apparatus for analyzing solution components and by which the apparatus is provided with portability facilitating access to a spot outside a laboratory to perform an instant sample analysis.

Another object of the present invention is to provide an apparatus for solution component analysis and fabricating method thereof, by which an optical system configuration for sample analysis can be simplified in a manner of facilitating an optical transfer by forming a transparent silicon oxide ($SiO_2$) layer between a micro channel of the apparatus and an optical fiber to insert the optical fiber therein.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an apparatus for solution component analysis according to the present invention comprises a plurality of grooves, which is formed on a substrate, comprising a plurality of sample inlets; a plurality of microchannels connected to a plurality of the sample inlets to enable a plurality of samples to flow therein, respectively; a mixing channel communicating with a plurality of the microchannels to mix a plurality of the samples within a plurality of the microchannels; a reaction channel enabling the samples mixed in the mixing channel to react; a measurement channel measuring the samples having reacted in the reaction channel; and an outlet discharging the samples having completed a measurement in the measurement channel, wherein the measurement channel comprises an input microchannel connected to the reaction channel to receive the reaction-completed samples from the reaction channel, a straight microchannel enabling the reaction-completed samples via the input microchannel to flow straight and to transmit a light in a direction that the reaction-completed samples flow, and an output microchannel outputting the samples having passed through the straight microchannel to the outlet; optical fiber insertion grooves provided on the substrate to communicate with both ends of the straight microchannel, respectively; first and second optical fibers inserted to be fixed in the optical fiber insertion grooves so that the light can be inputted and outputted via the first and second optical fibers, respectively; and a transparent layer between the measurement channel and each of the optical fiber insertion grooves.

In another aspect of the present invention, a method of fabricating an apparatus for solution component analysis comprises a first step of forming a plurality of grooves and optical fiber insertion grooves to insert a plurality of optical fibers therein, respectively, on a first substrate, wherein a plurality of the grooves comprise a plurality of sample inlets, a plurality of microchannels connected to a plurality of the sample inlets, respectively, a mixing channel communicating with a plurality of the microchannels, a reaction channel communicating with the mixing channel, a measurement channel communicating with the reaction channel, and an outlet communicating with the measurement channel; a second step of bonding a second substrate having perforated holes for solution injection and discharge onto the first substrate, wherein the perforated holes correspond to the sample injection inlet and the outlet, respectively; and a third step of inserting first and second optical fibers in the optical fiber insertion grooves, respectively.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
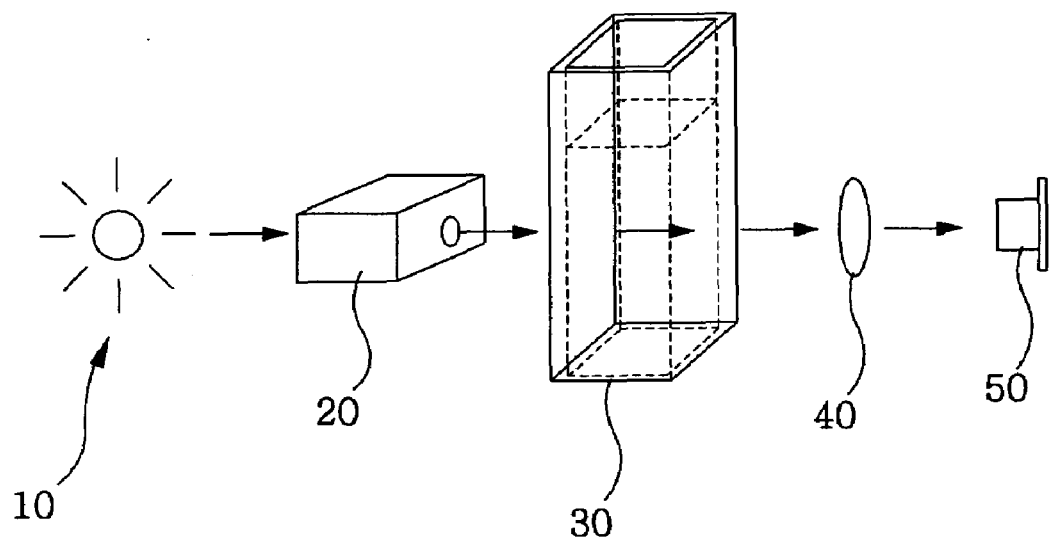
FIG. 1 is a schematic diagram of a solution component analyzing device according to a related art.
Figure 2:
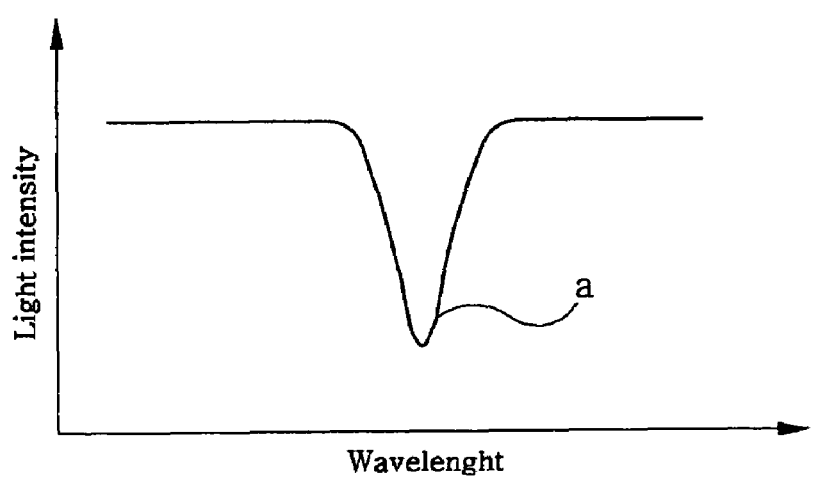
FIG. 2 is an exemplary graph of measurement by a solution component analyzer according to prior art.
Figure 3:
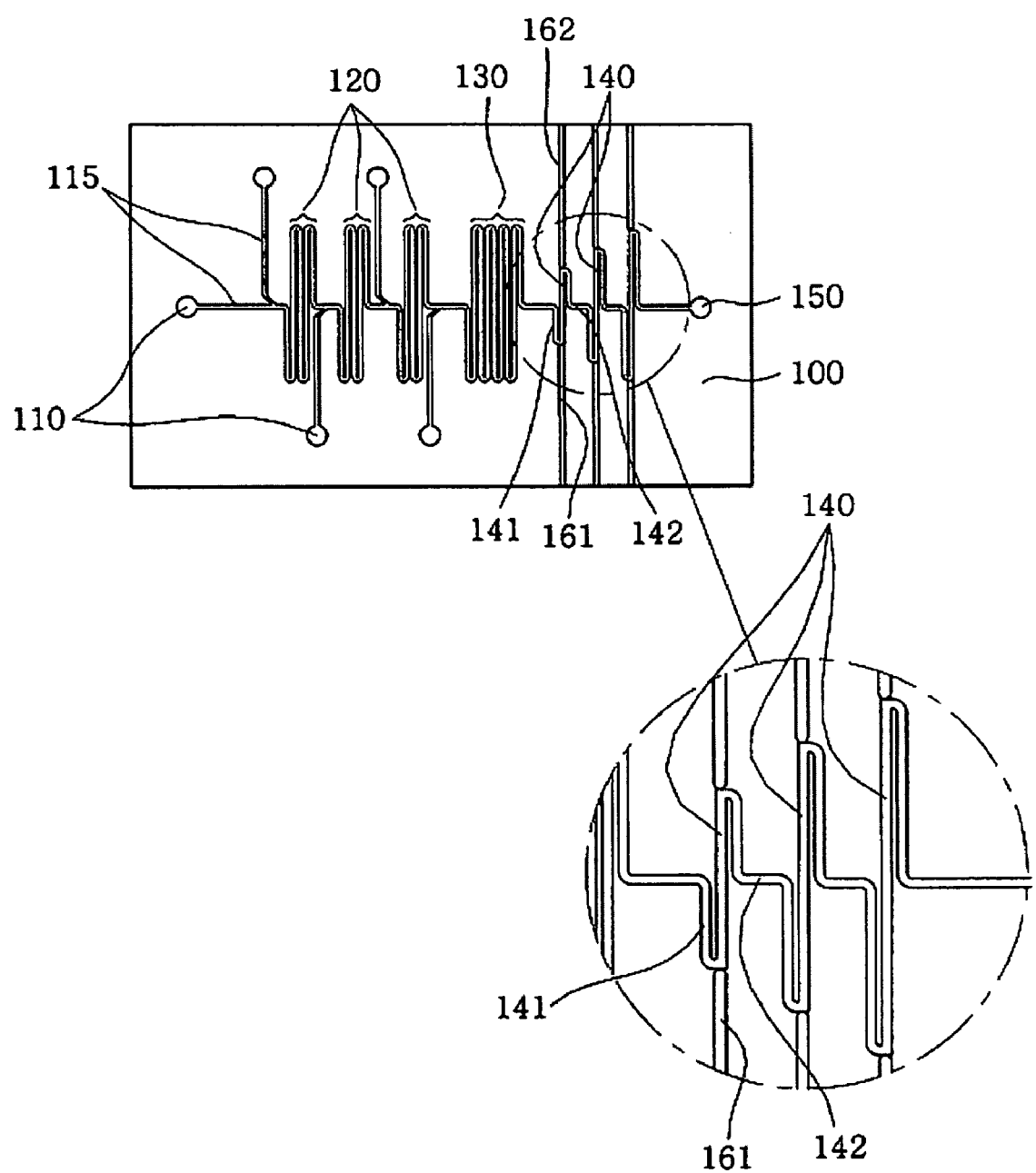
FIG. 3 is a layout of an apparatus for solution component analysis according to the present invention.

FIG. 3 is a layout of an apparatus for solution component analysis according to the present invention.

Referring to FIG. 3, an apparatus for solution component analysis according to the present invention comprises a plurality of grooves formed on a substrate. A plurality of the grooves comprise a plurality of sample inlets 110, a plurality of microchannels 115 connected to a plurality of the sample inlets 110 to enable a plurality of samples to flow therein, respectively, a mixing channel 120 connected to a plurality of the microchannels 115 to mix a plurality of the samples, a reaction channel 130 enabling the samples mixed in the mixing channel 120 to react, a measurement channel 140 measuring the samples having reacted in the reaction channel 130, and an outlet 150 discharging the samples having completed a measurement in the measurement channel. The measurement channel 140 comprises an input microchannel 141 connected to the reaction channel 130 to receive the reaction-completed samples from the reaction channel 130, at least one straight microchannel 140 enabling the reaction-completed samples via the input microchannel 141 to flow straight and to transmit a light in a direction that the reaction-completed samples flow, and an output microchannel 142 outputting the samples having passed through the straight microchannel 140 to the outlet 150. Optical fiber insertion grooves 161 and 162 are provided on the substrate to be connected to both ends of each of the at least one or more straight microchannels 140, respectively. And, first and second optical fibers are inserted to be fixed in the optical fiber insertion grooves 161 and 162 so that the light can be inputted and outputted via the first and second optical fibers, respectively. Moreover, the at least one or more straight microchannels 140 differ from each other in length so that a plurality of the straight microchannels can communicate with each other.

Thus, if photo-absorption of the measurement sample is high and if a length of the measurement channel is long, the light incident on the measurement sample solution is entirely absorbed in the sample solution, whereby the variation of the light intensity cannot be measured in the light-receiving unit.

In this case, the straight microchannel 140 having a shorter length is selected to lower the photo-absorption, whereby the variation of the light intensity according to the photo-absorption can be measured.

And, if photo-absorption of the measurement sample is low and if the length of the measurement channel is short, the light incident on the measurement sample solution is barely absorbed in the sample solution, whereby the variation of the light intensity cannot be measured in the light-receiving unit.

In this case, the straight microchannel 140 having a longer length is selected to raise the photo-absorption, whereby the variation of the light intensity according to the photo-absorption can be measured.

Figure 4:
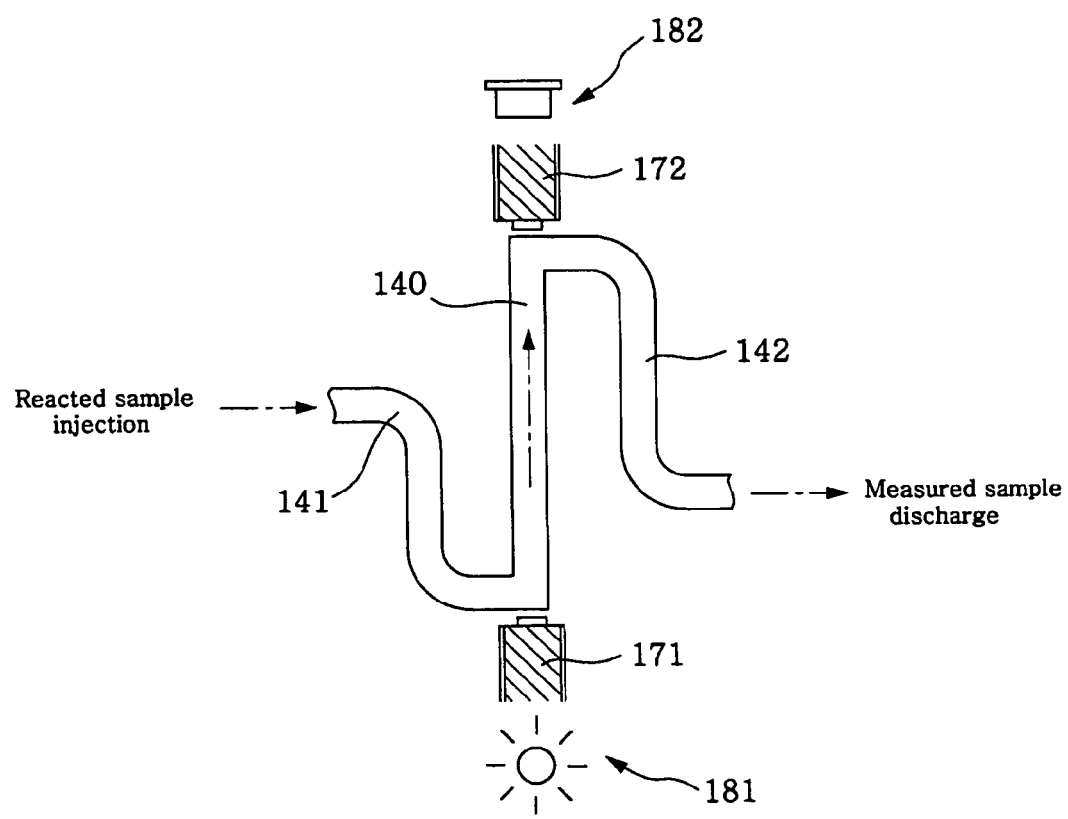
FIG. 4 is a diagram for explaining a method of measuring a component and concentration of a sample solution using a measurement channel and optical fibers of an apparatus for solution component analysis according to the present invention.

FIG. 4 is a diagram for explaining a method of measuring a component and concentration of a sample solution using a measurement channel and optical fibers of an apparatus for solution component analysis according to the present invention. Referring to FIG. 4, the input microchannel 141 receives the reacted sample from the reaction channel. When the reacted sample having passed through the input microchannel 141 straightly flows through the straight microchannel 140, the light irradiated from the light source 181 is passed through a first optical fiber 171 to pass through the sample which is flowing in the straight microchannel 140.

In doing so, the sample solution contains a substance of a specific component so that a pattern variation of a photoabsorption spectrum occurs in a specific wavelength band of the light that is passing through the sample solution.

Subsequently, a second optical fiber 172 receives the light having passed through the sample to transfer to the light-receiving unit 182. In doing so, the light-receiving unit 182 comprising a light-receiving sensor or spectrometer measures the variation of the light intensity according to the wavelength of the light having passed through the sample.

Thereafter, the sample having completed its measurement in the straight microchannel 140 is discharged from the outlet via the output microchannel 142.

FIGS. 5A to 5D are cross-sectional diagrams of a method of fabricating an apparatus for solution component analysis according to the present invention.

Figure 5A:
FIGS. 5A to 5D are cross-sectional diagrams of a method of fabricating an apparatus for solution component analysis according to the present invention.

Referring to FIG. 5A, a first substrate 200 is prepared.

Figure 5B:
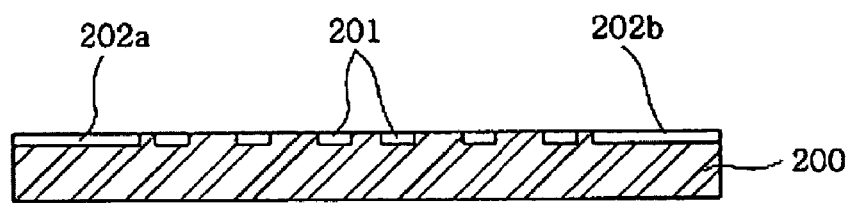

Referring to FIG. 5B, a plurality of '⌑' type microchannel grooves 201 including sample injection inlets, microchannels connected to the sample injection inlets, respectively, a mixing channel communicating with the microchannels, a reaction channel communicating with the mixing channel, a measurement channel communicating with the reaction channel, and an outlet connected to the measurement channel and '⌑' type optical fiber insertion grooves 202a and 202b to insert and fix optical fibers thereto, respectively, are simultaneously formed on the first substrate 200.

In this case, the first substrate 200 is a silicon substrate and the microchannel grooves 201 and the optical fiber insertion grooves 202a and 202b are formed by etching the silicon substrate vertically using silicon deep etching.

Figure 5C:
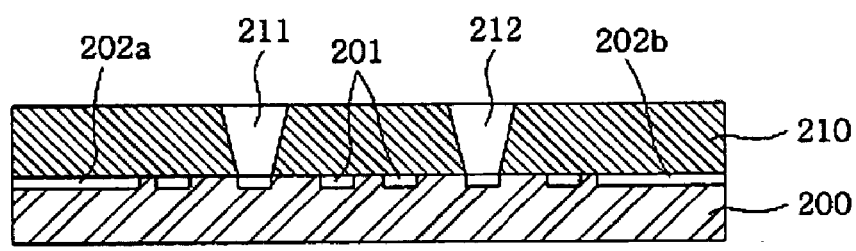

Referring to FIG. 5C, a second substrate 210 having perforated holes 211 and 212 for solution injection and discharge is attached on the first substrate 200 on which the process in FIG. 5B has been performed so that the perforated holes 211 and 212 can correspond to the microchannel grooves of the sample inlet and outlet on the first substrate 200.

In doing so, the second substrate 210 can be formed of glass or PDMS (polydimethylsiloxane). In case that the second substrate 210 is a glass substrate, the second substrate 210 is assembled to the first substrate 200 by anodic bonding so that the sample can flow inside the microchannel grooves 201.

Figure 5D:
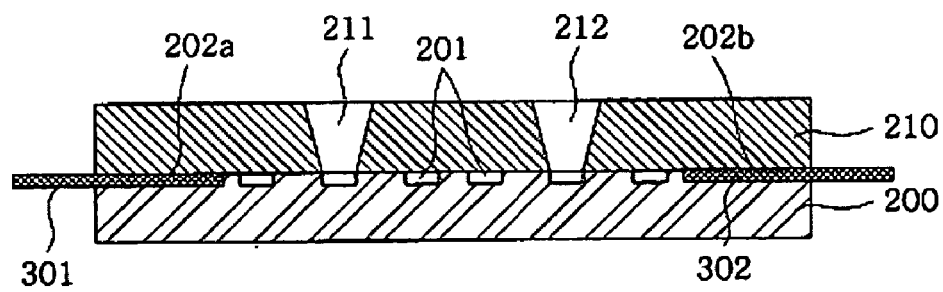

Referring to FIG. 5D, first and second optical fibers 301 and 302 are inserted in the optical fiber insertion grooves 202a and 202b, respectively.

Figure 6A:
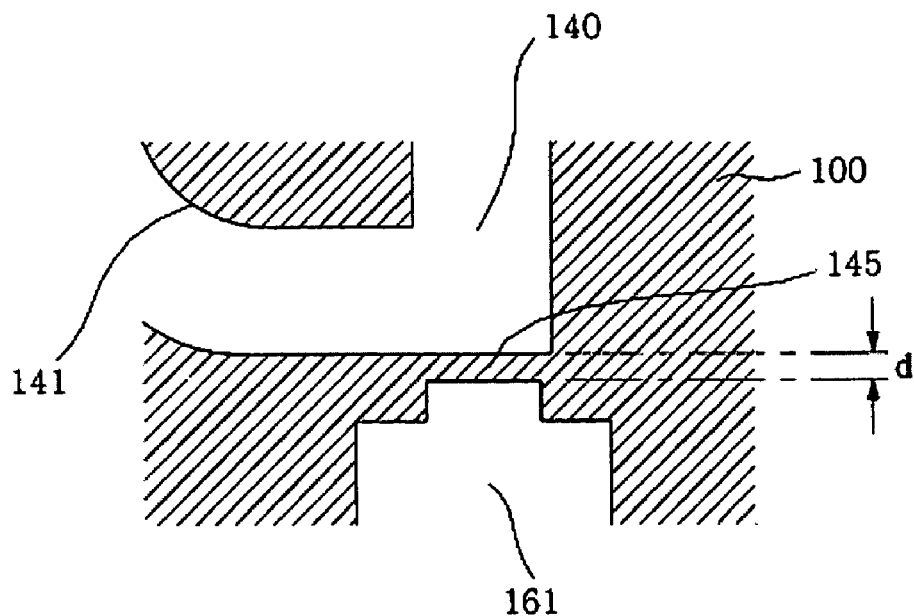
FIG. 6A and FIG. 6B are magnified layouts for explaining a process of forming a transparent silicon oxide ($SiO_2$) layer between a measurement channel and an optical fiber insertion groove.
Figure 6B:
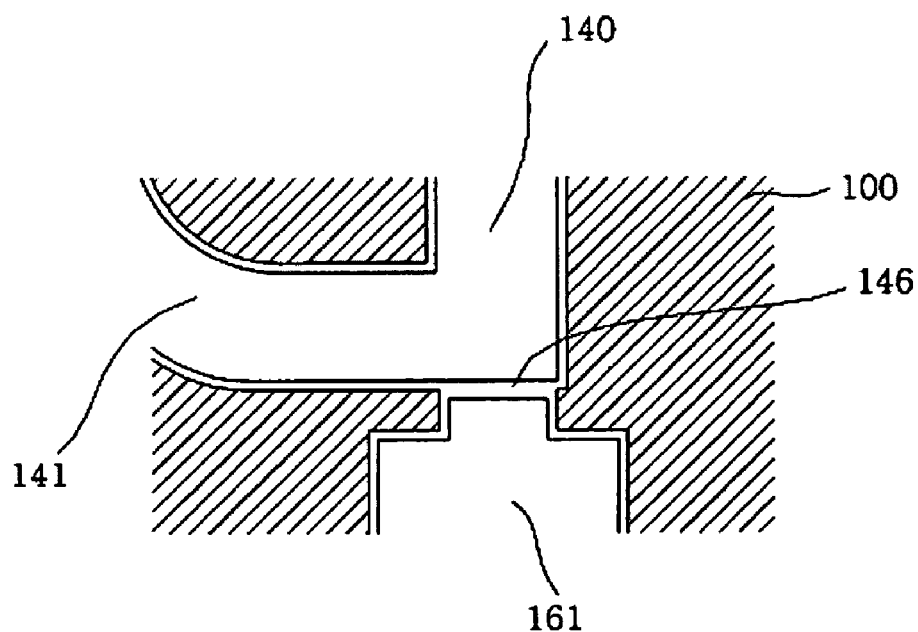

FIG. 6A and FIG. 6B are magnified layouts for explaining a process of forming a transparent silicon oxide ($SiO_2$) layer between a measurement channel and an optical fiber insertion groove.

In case that the substrate 100 of the apparatus for solution component analysis according to the present invention is a silicon substrate, FIG. 6A shows that the measurement channel 140, input microchannel 141, and optical insertion groove 161 are formed by etching the silicon substrate vertically using deep etching.

In this case, a silicon layer 145 having a thickness 'd' of several micrometers is formed between the measurement channel 140 and the optical fiber insertion groove 161.

Since the silicon layer 145 has a very small light transmittance in a visible ray band, the optical transmission loss increases in the process of transferring the light coming out of the optical fiber to the measurement channel 140.

In order to solve the problem, the silicon substrate is oxidized to form a transparent layer as the silicon layer 145 to provide a high light transmittance in the visible ray band.

Referring to FIG. 6B, by the oxidation of the silicon substrate, a silicon oxide layer 146 is formed at an interface between the measurement channel 140 and the optical fiber insertion groove 161 the moment the silicon layer 145 is turned into the silicon oxide ($SiO_2$) layer 146.

Therefore, the transparent layer having a high light transmittance in the visible ray band can be provided between the measurement channel 140 and the optical fiber insertion groove 161.

And, the transparent silicon oxide layer 146 prevents the sample solution from leaking toward the optical fiber from the measurement channel 140 and is operative in transferring the light coming out of the optical fiber to the measurement channel 140 smoothly.

Figure 7:
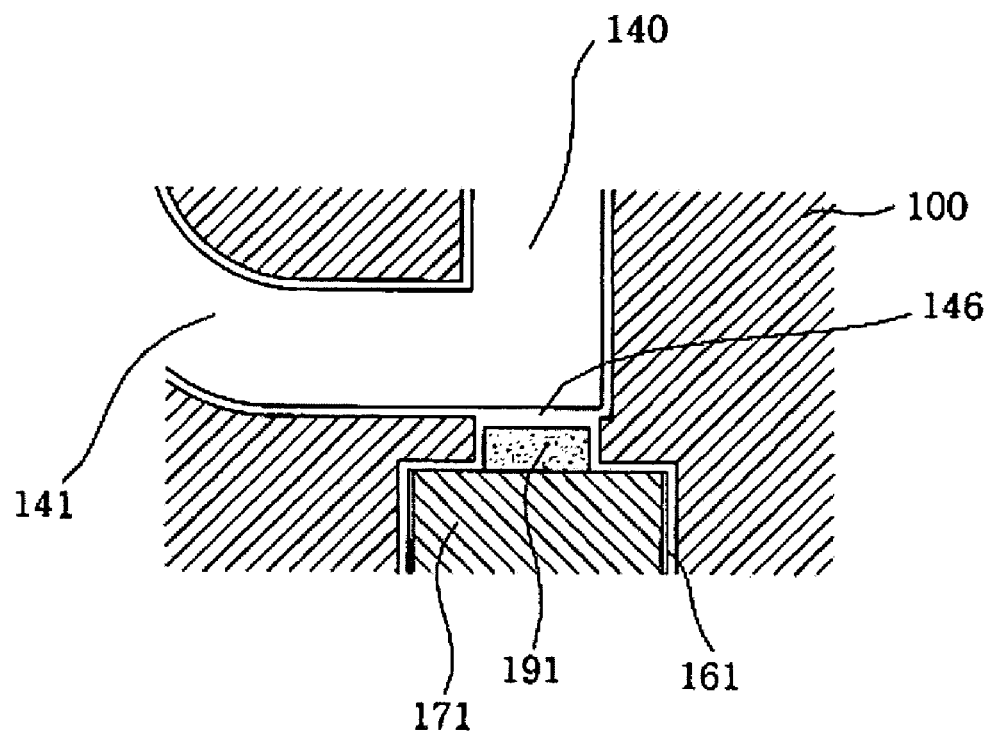
FIG. 7 is a magnified layout of an optical fiber inserted in an optical fiber insertion groove according to the present invention.

FIG. 7 is a magnified layout of an optical fiber inserted in an optical fiber insertion groove according to the present invention. Referring to FIG. 7, since the transparent silicon oxide layer 146 has the length of several micrometers, distortion of the layer 146 may be caused by the layer stress on forming the silicon oxide layer.

In order to minimize the distortion, an opening area of the transparent silicon oxide layer 146 formed in a direction of the optical fiber is formed as small as possible within a range failing to affect the light transfer of the optical fiber.

After the optical fiber 171 has been inserted in the optical fiber insertion groove 161, in order to prevent the transparent silicon oxide layer 146 from being broken by the pressure of the sample solution flowing in the measurement channel 140 and to minimize Fresnel Reflection between the silicon oxide layer 146 and the optical fiber 171, a space between the transparent silicon oxide layer 146 and the optical fiber 171 is filled up with UV-hardening type transparent epoxy 191.

Figure 8:
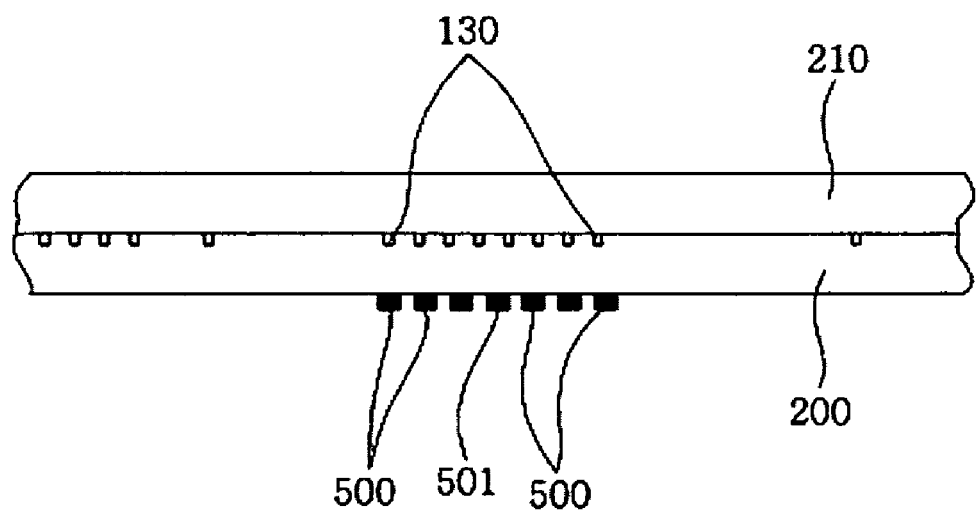
FIG. 8 is a cross-sectional diagram of a micro heater and temperature sensor provided beneath a substrate corresponding to an area where a reaction channel of an apparatus for solution component analysis according to the present invention exists.

FIG. 8 is a cross-sectional diagram of a micro heater and temperature sensor provided beneath a substrate corresponding to an area where a reaction channel of an apparatus for solution component analysis according to the present invention exists.

Referring to FIG. 8, in order to enable chemical reaction to occur more favorably by maintaining a uniform temperature of the sample solution within the reaction channel 130, a micro heater 500 and a temperature sensor 501 are further provided beneath the substrate 100 corresponding to the area where the reaction channel 130 exists.

Since the reaction channel is constructed with a microchannel, the mixed sample solution may proceed to the measurement channel from the reaction channel to be measured before reacting sufficiently. Hence, in order to enable the sample solution passing through the reaction channel to react chemically and sufficiently in a short time, the micro heater 500 is provided to the bottom of the substrate 100 and the temperature sensor 501 is provided to control the temperature of the micro heater 500 as well.

As mentioned in the foregoing description of the apparatus for solution component analysis according to the present invention, the mixing, reaction, and measurement channels are continuously connected in turn, whereby it is possible to considerably reduce the size of the microanalysis apparatus.

And, the transparent silicon oxide layer is formed between the measurement channel and the optical fiber to facilitate the light transfer via the inserted optical fibers, thereby enabling to simplify the configuration of the optical system for sample analysis.

Accordingly, in the present invention, the mixing channel, reaction channel, and measurement channel are formed as a continuous micro-groove on one substrate to implement the miniature apparatus for analyzing solution components and the apparatus is provided with portability facilitating access to a spot outside a laboratory to perform an instant sample analysis. Moreover, in the present invention, an optical system configuration for sample analysis can be simplified in a manner of facilitating an optical transfer by forming a transparent silicon oxide layer between a micro channel of the apparatus and an optical fiber to insert the optical fiber therein.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. An apparatus for solution component analysis, comprising:
    A plurality of grooves, which are formed on a substrate, comprising:
    a plurality of sample inlets;
    a plurality of microchannels connected to the plurality of sample inlets to enable a plurality of samples to flow therein, respectively;
    a mixing channel communicating with the plurality of microchannels to mix the plurality of samples within the plurality of microchannels;
    a reaction channel enabling the samples mixed in the mixing channel to react;
    a measurement channel measuring the samples having reacted in the reaction channel; and
    an outlet discharging the samples having completed a measurement in the measurement channel in the measurement channel, wherein the measurement channel comprises an input microchannel connected to the reaction channel to receive the reaction-completed samples from the reaction channel, a straight microchannel enabling the reaction-completed samples from the reaction channel, a straight microchannel enabling the reaction-completed samples via the input microchannel to flow straight and to transmit a light in a direction that the reaction-completed samples flow, and an output microchannel outputting the samples having passed through the straight microchannel to the outlet;
    optical fiber insertion grooves provided on the substrate to communicate with both ends of the straight microchannel, respectively;
    first and second optical fibers inserted and fixed in the optical fiber insertion grooves so that the light can be inputted and outputted via the first and second optical fibers, respectively; and
    a transparent layer between the measurement channel and each of the optical fiber insertion grooves.

2. The apparatus of claim 1, further comprising:
    a light source applying the light to the first optical fibers and a light-receiving unit receiving the light outputted to the second optical fibers.

3. The apparatus of claim 1, wherein the transparent layer is a silicon oxide layer.

4. The apparatus of claim 3, wherein UV-hardening type transparent epoxy is provided between the transparent silicon oxide layer and each of the first and second optical fibers.

5. The apparatus of one of claims 1 to 4, wherein a micro heater and a temperature sensor are further provided to a bottom of the substrate corresponding to an area where the reaction channel exists.

6. The apparatus of one of claims 1 to 4, wherein a separate substrate provided with perforated holes corresponding to at least one of the plurality of sample inlets and the outlet, respectively is bonded onto the substrate.

7. The apparatus of claim 1, wherein the straight microchannel comprises a plurality of straight channels that communicate with each other but differ from each other in length.

8. A method of fabricating an apparatus for solution component analysis, comprising:
    a first step of forming a plurality of grooves and optical fiber insertion grooves to insert a plurality of optical fibers therein, respectively, on a first substrate, wherein a plurality of the grooves comprise a plurality of sample inlets, a plurality of microchannels connected to a plurality of the sample inlets, respectively, a mixing channel communicating with a plurality of the microchannels, a reaction channel communicating with the mixing channel, a measurement channel communicating with the reaction channel, and an outlet communicating with the measurement channel;
    a second step of bonding a second substrate having perforated holes for solution injection and discharge onto the first substrate wherein the perforated holes correspond to the sample injection inlet and the outlet, respectively; and
    a third step of inserting first and second optical fibers in the optical fiber insertion grooves, respectively.

9. The method of claim 8, wherein in the first step, the measurement channel comprises an input microchannel connected to the reaction channel to receive the reaction-completed samples from the reaction channel, a straight microchannel enabling the reaction-completed samples via the input microchannel to flow straight and to transmit a light in a direction that the reaction-completed samples flow, and an output microchannel outputting the samples having passed through the straight microchannel to the outlet and wherein the optical fiber insertion grooves are provided on the first substrate to communicate with both ends of the straight microchannel, respectively.

10. The method of claim 9, the first step further comprising the steps of:
    forming a silicon layer between the measurement channel and each of the optical fiber insertion grooves; and
    oxidizing the silicon layer to form a transparent silicon oxide layer.

11. The method of claim 8, wherein in the second step, the second substrate is formed of a material selected from the group comprising glass and PDMS (polydimethylsiloxane) and wherein if the second substrate is formed of the glass, the first and second substrates are bonded to each other by anodic bonding.

* * * * *